United States Patent [19]

Yokoi et al.

[11] Patent Number: 4,904,809
[45] Date of Patent: Feb. 27, 1990

[54] PLATINUM COMPLEX

[75] Inventors: Koichi Yokoi, Kashiwa; Kinichi Mogi, Abiko; Kazuhiko Irinoda, Chiba; Hidehiko Kohya, Narita; Susumu Sato, Shisui; Tatsuhiko Katori, Tone, all of Japan

[73] Assignee: SS Pharmaceutical Co., Ltd., Tokyo, Japan

[21] Appl. No.: 245,222

[22] Filed: Sep. 16, 1988

[30] Foreign Application Priority Data

Sep. 25, 1987 [JP] Japan ................................ 62-241542

[51] Int. Cl.$^4$ ............................................. C07F 15/00
[52] U.S. Cl. .................................................. 556/137
[58] Field of Search ................... 556/137, 40; 514/492

[56] References Cited

U.S. PATENT DOCUMENTS 4,500,465 2/1985 Amundsen et al. ................... 556/17

FOREIGN PATENT DOCUMENTS 0055300 4/1981 European Pat. Off. .
0098135 6/1983 European Pat. Off. .
0166366 6/1985 European Pat. Off. .
0186085 12/1985 European Pat. Off. .
0219936 8/1986 European Pat. Off. .
0228298 12/1986 European Pat. Off. .
0079994 5/1983 Japan ................................ 556/137

OTHER PUBLICATIONS

CHEMICO—BIOLOGICAL INTERACTIONS, vol. 46, No. 2, 1983, pp. 219-232, Elsevier Scientific Publishers Ireland Ltd., GB; B. Das SARMA et al.: "Platinum Complexes with Anticancer Potential and Their Evaluation by a Colorimetric Lambda Prophage Induction Assay", *p. 222, compound 24*.
Appleton, T. G. and Hall, J. R. in *Inorganic Chemistry*, vol. 11, No. 1, 1972, pp. 112-117.

Primary Examiner—John Doll
Assistant Examiner—Stuart L. Hendrickson
Attorney, Agent, or Firm—Oblon, Spivak, McClelland, Maier & Neustadt

[57] ABSTRACT

A platinum complex having a superior antitumor activity is disclosed. The platinum complex has a structure represented by the formula:

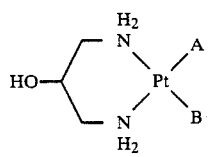

wherein A and B independently represent a lower alkanoyloxy group which may have a halogen atom substituent, or in combination represent a group:

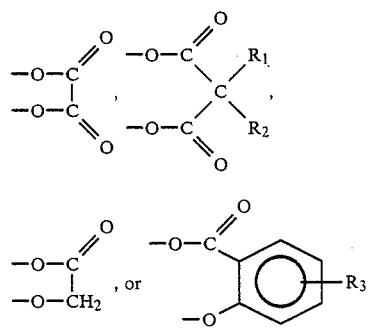

wherein $R_1$ and $R_2$ independently represent a hydrogen atom, a hydroxyl group, or a lower alkyl group, or in combination with each other and with the adjacent carbon atom a cyclobutane ring, and $R_3$ represents a hydrogen atom, a lower alkyl group, a lower alkoxy group, a halogen atom, a sulfo group, or nitro group.

1 Claim, No Drawings

PLATINUM COMPLEX

BACKGROUND OF THE INVENTION

1. Field of the Invention

This invention relates to a platinum complex having a superior antitumor activity.

2. Description of the Background

Cisplatin, which is a platinum complex reported by Rosenberg et al. as a novel antitumor agent in 1969 [*Nature*, 222, 385 (1969)] has a wide antitumor spectrum and is used especially as a antitumor agent exhibiting a remarkable effect particularly on genitalia cancer, bladder cancer, and head and neck cancer, or the like. There are a number of studies on platinum complexes other than cisplatin. They are reported for instance in Japanese Patent Laid-open No. 31648/1978, Japanese Patent Laid-open No. 77694/1982, and the like.

The aforementioned cisplatin is commercially sold as a antitumor agent. The compound, however, has a high toxicity to kidney and other organs, and thus a limitation is imposed to its use. The purpose of the invention is to provide a platinum complex with a superior antitumor activity and yet exhibits a lower degree of toxicity.

The inventors have synthesized various platinum complexes having 1,3-diamino-2-propanol as a ligand and studied their pharmaceutical effects. As a result, the inventors have found that a platinum complex represented by the following formula (I) has advantages of a superior antitumor activity, a low toxicity, and high solubility in water. The finding has led to the completion of this invention.

SUMMARY OF THE INVENTION

Accordingly, an object of this invention is to provide a platinum complex represented by the following formula (I):

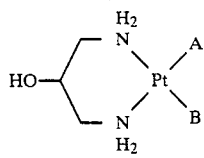

wherein A and B independently represent a lower alkanoyloxy group which may have a halogen atom substituent, or in combination represent a group:

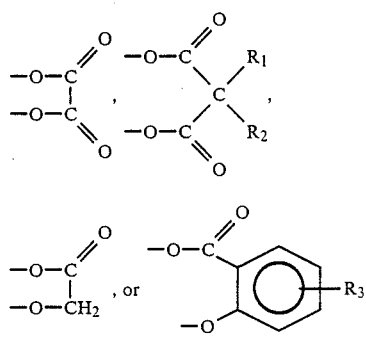

wherein $R_1$ and $R_2$ independently represent a hydrogen atom, a hydroxyl group, or a lower alkyl group, or in combination with each other and with the adjacent carbon atom a cyclobutane ring, and $R_3$ represents a hydrogen atom, a lower alkyl group, a lower alkoxy group, a halogen atom, a sulfo group, or nitro group.

Other objects, features and advantages of the invention will hereinafter become more readily apparent from the following description.

DETAILED DESCRIPTION OF THE INVENTION AND PREFERRED EMBODIMENTS

In formula (I), a lower alkanoyloxy group may be, for example, an alkanoyloxy group having 2 to 5 carbon atoms, and a lower alkyl and lower alkoxy groups may be those having 1 to 5 carbon atoms.

The platinum complex of this invention can be prepared, for example, according to the following reaction scheme.

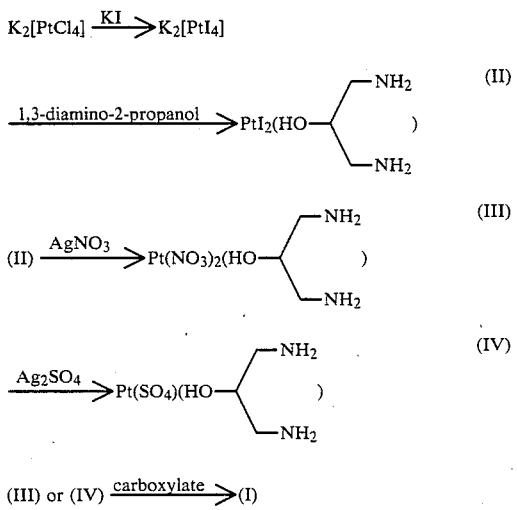

Specifically, according to the above reaction formulae, potassium iodide is added into an aqueous solution of potassium tetrachloroplatinate to produce an aqueous solution of potassium tetraiodoplatinate. To this solution 1,3-diamino-2-propanol is added and reacted to give the compound (II). This compound (II) in an aqueous solution is then treated with silver nitrate to prepare a dinitrato complex (III), or with silver sulfate to prepare sulfato complex (IV). The target compound (I) of this invention is prepared by reacting the dinitrato complex (III) or sulfato complex (IV) with a carboxylate.

Given as examples of carboxylates used in the above reaction are salts of monocarboxylic acid such as acetic acid, propionic acid, butylic acid, chloroacetic acid, bromoacetic acid, or the like; dicarboxylic acid such as oxalic acid, malonic acid, hydoxymalonic acid, methylmalonic acid, dimethylmalonic acid, diethylmalonic acid, 1,1-cyclobutanedicarboxylic acid, or the like; glycolic acid, salicylic acid, 3-methylsalicylic acid, 4-methylsalicylic acid, 3-methoxysalicylic acid, 4-methoxysalicylic acid, 5-methoxysalicylic acid, 5-nitrosalicylic acid, 3-chlorosalicylic acid, 4-chlorosalicylic acid, 5-chlorosalicylic acid, 3-sulfosalicylic acid, 5-sulfosalicylic acid, and the like.

Other features of the invention will become apparent in the course of the following description of the exemplary embodiments which are given for illustration of the invention and are not intended to be limiting thereof.

EXAMPLES

Example 1

Preparation of (1,3-diamino-2-propanol)oxalatoplatinum (II) (Compound No. 1)

Into 80 ml of water 4.15 g of potassium tetrachloroplatinate was dissolved. To the solution was added 16.6 g of potassium iodide and the mixture was stirred for 1 hour at room temperature to produce an aqueous solution of potassium tetraiodoplatinate. To this solution 5 ml of 900 mg 1,3-diamino-2-propanol aqueous solution was added dropwise, and the mixture was stirred at 60° C. for 5 minutes. The deposited crystals were collected by filtration and the filtrate was washed with water, acetone, and then ether, and dried in vacuo to obtain 4.72 g of yellow crystals of (1,3-diamino-2-propanol)cis-diiodoplatinum (II) at a yield of 88%.

1.07 g of cis-diido(1,3-diamino-2-propanol)platinum (II) thus prepared was suspended into 30 ml of water and to the suspension was added 0.68 g of silver nitrate dissolved into 10 ml of water. The mixture was stirred at room temperature for 3 hours. The produced silver iodide was removed by filtration. To the filtrate 0.368 g of potassium oxalate monohydrate was added and the mixture was stirred at 60° C. for 3 hours. After the reaction, the reaction mixture was cooled at 0° C. The deposited crystals were collected by filtration, washed with a small amount of water, methanol, then ether, and dried in vacuo to obtain 604 mg of Compound No. 1 in a form of colorless crystals at a yield of 81%.

Example 2

Synthesis of (1,3-diamino-2-propanol)malonatoplatinum (II) (Compound No. 2)

Into 40 ml of water 1.07 g of (1,3-diamino-2-propanol) cis-diiodoplatinum (II) prepared in Example 1 was suspended. To the suspension waes added 0.62 g of silver sulfate dissolved into 10 ml of water. The mixture was stirred at room temperature for 3 hours. The produced silver iodide was removed by filtration. The filtrate was condensed to 15 ml volume and to this was added 0.21 g of malonic acid in 4 ml of 1N sodium hydroxide solution. The mixture was left at room temperature for 3 days and the reaction mixture was cooled at 0° C. The deposited crystals were collected by filtration, washed with a small amount of water, ethanol, then ether, and dried in vacuo to obtain 0.59 g of Compound No. 2 in a form of colorless crystal at a yield of 75%.

Example 3

Synthesis of (1,1-cyclobutanedicarboxylato)(1,3-diamino-2-propanol) platinum (II) (Compound No. 3)

Into 60 ml of water 1.62 g of (1,3-diamino-2-propanol) cis-diiodoplatinum (II) prepared in Example 1 was suspended. To the suspension was added 1.02 g of silver nitrate dissolved into 10 ml of water. The mixture was stirred at room temperature for 3 hours. The produced silver iodide was removed by filtration. To the filtrate was added 0.43 g of 1,1-cyclobutanedicarboxylic acid in 6 ml of 1N sodium hydroxide solution. The mixture was reacted at room temperature for 1 day. After the reaction, reaction mixture was condensed and the condensate was cooled at 0° C. The deposited crystals were collected by filtration, washed with a small amount of cold water, acetone, then ether, and dried in vacuo to obtain 0.98 g of Compound No. 3 in a form of colorless crystal at a yield of 76%.

Examples 4-7

Compounds No. 4-7 were prepared in the same manner as in Example 3.

Compound No. 4:
(1,3-diamino-2-propanol)hydroxymalonatoplatinum (I)

Compound No. 5:
(1,3-diamino-2-propanol)methylmalonatoplatinum (II)

Compound No. 6:
(1,3-diamino-2-propanol)dimethylmalonatoplatinum (II)

Compound No. 7:
(1,3-diamino-2-propanol)diethylmalonatoplatinum (II)

Example 8

Synthesis of (1,3-diamino-2-propanol)(glycolato-O,O')-platinum (II) (Compound No. 8)

The same procedure as in Example 3 was carried out, except that 0.23 g of glycolic acid was used instead of 1,1-cyclobutanedicarboxylic acid to produce 0.81 g of Compound No. 8 as colorless crystals at a yield of 75%.

Example 9

Synthesis of (1,3-diamino-2-propanol)(salicylato-O,O')-platinum (II) (Compound No. 9)

The same procedure as in Example 1 was carried out, except that 0.48 g of sodium salicylate was used instead of potassium oxalate monohydrate to produce 0.92 g of Compound No. 9 as colorless crystals at a yield of 73%.

Examples 10-11

Compound Nos. 10 and 11 were prepared in the same manner as in Example 9.

Compound No. 10:
(1,3-diamino-2-propanol)(5-methoxysalicylato-O,O') platinum (II)

Compound No. 11:
(1,3-diamino-2-propanol)(5-sulfosalicylato-O,O') platinum (II)

Example 12

Synthesis of bis(chloroacetato)(1,3-diamino-2-propanol) platinum (II) (Compound No. 12)

The same procedure as in Example 3 was carried out, except that 0.57 g of chloroacetic acid was used instead of 1,1-cyclobutanedicarboxylic acid to produce 0.99 g of Compound No. 12 as colorless crystals at a yield of 70%.

Physicochemical characteristics of Compound Nos. 1 to 12 thus prepared are shown in Table 1.

TABLE 1

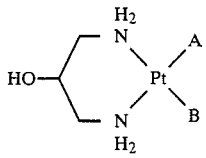 (I)

| Compound No. | In Formula (I) A, B | IR $\nu_{max}^{KBr}$ cm$^{-1}$ | FAB-MS ($^{195}$Pt) (M + H)$^+$ | | Elemental Analysis Calculated (Found) C  H  N | | | Characteristics Melting Point (°C.) |
|---|---|---|---|---|---|---|---|---|
| 1 | | 3400, 3250, 3150 1700, 1670, 1390 | 374 | C$_5$H$_{10}$N$_2$O$_5$Pt | 16.09 (15.91 | 2.70 2.64 | 7.51 7.48) | Colorless crystals 185–197 (decomp.) |
| 2 | | 3300, 3230, 3130 1670, 1640, 1620 1590, 1405 | 388 | C$_6$H$_{12}$N$_2$O$_5$Pt | 18.61 (18.45 | 3.12 2.99 | 7.23 7.06) | Colorless crystals 223–233 (decomp.) |
| 3 | | 3450, 3250, 3150 1630, 1380 | 428 | C$_9$H$_{16}$N$_2$O$_5$Pt | 25.30 (25.08 | 3.77 3.97 | 6.56 6.40) | Colorless crystals 225–233 (decomp.) |
| 4 | | 3500, 3400, 3220 3150, 1640–1680 | 404 | C$_6$H$_{12}$N$_2$O$_6$Pt | 17.87 (17.71 | 3.00 2.84 | 6.95 7.19) | Colorless crystals 215–230 (decomp.) |
| 5 | | 3450, 3220, 3120 1670, 1630, 1400 1390 | 402 | C$_7$H$_{14}$N$_2$O$_5$Pt | 20.95 (20.85 | 3.52 3.67 | 6.98 6.73) | Colorless crystals 195–210 (decomp.) |
| 6 | | 3400, 3250, 3150 1620, 1600 | 416 | C$_8$H$_{16}$N$_2$O$_5$Pt | 23.14 (23.07 | 3.88 3.89 | 6.75 6.65) | Colorless crystals 205–215 (decomp.) |
| 7 | | 3600, 3450, 3210 1615, 1560 | 444 | C$_{10}$H$_{20}$N$_2$O$_5$Pt | 27.09 (27.01 | 4.55 4.59 | 6.32 6.23) | Colorless crystals 215–230 (decomp.) |
| 8 | | 3530, 3350, 3200 3100, 1620, 1590 1370 | 360 | C$_5$H$_{12}$N$_2$O$_4$Pt | 16.72 (16.81 | 3.37 3.43 | 7.80 7.67) | Colorless crystals 180–189 (decomp.) |

TABLE 1-continued

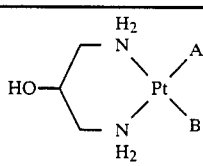

(I)

| Compound No. | In Formula (I) A, B | IR $\nu_{max}^{KBr}$ cm$^{-1}$ | FAB-MS ($^{195}$Pt) (M + H)$^+$ | Elemental Analysis Calculated (Found) | | | Characteristics Melting Point (°C.) |
|---|---|---|---|---|---|---|---|
| | | | | C | H | N | |
| 9 | (methyl 2,3-dihydroxybenzoate group) | 3450, 3250, 3150 1610, 1590 | 422 | C$_{10}$H$_{14}$N$_2$O$_4$Pt 28.51 (28.44 | 3.35 3.41 | 6.65 6.58) | Colorless crystals 240–255 (decomp.) |
| 10 | (methyl 2,3-dihydroxy-5-methoxybenzoate group) | 3450, 3250, 3150 1645, 1620 | 452 | C$_{11}$H$_{16}$N$_2$O$_5$Pt 29.27 (29.37 | 3.57 3.66 | 6.21 6.07) | Colorless crystals 145–155 (decomp.) |
| 11 | (methyl 2,3-dihydroxy-5-sulfobenzoate group) | 3450, 3250, 3150 1605 | 502 | C$_{10}$H$_{14}$N$_2$O$_7$PtS 23.96 (24.08 | 2.81 2.88 | 5.59 5.49) | Colorless crystals 220–235 (decomp.) |
| 12 | OCOCH$_2$Cl, OCOCH$_2$Cl | 3400, 3250, 3150 1630 | 472 | C$_7$H$_{14}$N$_2$O$_5$Cl$_2$Pt 17.81 (17.89 | 2.99 3.07 | 5.93 5.82) | Colorless crystals 115–130 (decomp.) |

EXPERIMENT EXAMPLES

Antitumor activity of the compound of this invention is now illustrated by an experimental example.

(Test Method)

CDF$_1$ male mice (age: 6 weeks) consisting of 6 per each group were provided to the test. 1×10$^6$ mouse L-1210 leukemia cells were intraperitoneally inoculated into each mouse. Starting from the first day of inoculation, each test compound dissolved into 0.5% CMC-Na containing 0.8% of sodium chloride was intraperitoneally administered to each mouse once a day for 5 consecutive days. Physiological saline was administered to the group of mice untreated by a test compound. Cisplatin and carboplatin, both are known compounds, were administered to the mice of the control groups.

Increase life span (ILS) was determined according to the following equation.

$$ILS = (T/C - 1) \times 100 (\%)$$

wherein T is average days of survival of the treated groups, and C is the corresponding average days of survival of the control groups.

The results are shown in Table 2.

TABLE 2

| Compound | Dose (mg/kg) | ILS (%) | Number of mice survived for 30 days or more |
|---|---|---|---|
| Compound No. 2 | 32 × 5 | >129 | 5 |
| Compound No. 3 | 8 × 5 | >143 | 6 |
| Cisplatin | 2 × 5 | >113 | 1 |
| Carboplatin | 16 × 5 | >109 | 3 |

The compound of this invention has a superior antitumor effect, exhibits a low toxicity, and is abundantly soluble in water, and thus is useful as antitumor agent.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. The compound which is bis(chloroacetato)(1,3-diamino-2-propanol)platinum (II).

* * * * *